(12) United States Patent
Thorne et al.

(10) Patent No.: US 11,433,390 B2
(45) Date of Patent: Sep. 6, 2022

(54) METHODS AND SYSTEMS FOR A CAPILLARY DEVICE

(71) Applicant: ION LLC, Portland, OR (US)

(72) Inventors: James Thorne, Portland, OR (US); Joshua King Hoyt, Portland, OR (US)

(73) Assignee: ION LLC, Portland, OR (US)

( * ) Notice: Subject to any disclaimer, the term of this patent is extended or adjusted under 35 U.S.C. 154(b) by 378 days.

(21) Appl. No.: 16/212,583

(22) Filed: Dec. 6, 2018

(65) Prior Publication Data

US 2019/0176144 A1 Jun. 13, 2019

Related U.S. Application Data

(60) Provisional application No. 62/595,999, filed on Dec. 7, 2017.

(51) Int. Cl.
*A61B 5/15* (2006.01)
*B01L 3/00* (2006.01)

(52) U.S. Cl.
CPC ........ *B01L 3/502* (2013.01); *A61B 5/150022* (2013.01); *A61B 5/150343* (2013.01); *A61B 5/150351* (2013.01); *B01L 3/50825* (2013.01); *A61B 5/150251* (2013.01); *A61B 5/150267* (2013.01); *B01L 2200/0605* (2013.01); *B01L 2300/042* (2013.01); *B01L 2300/047* (2013.01); *B01L 2400/0406* (2013.01)

(58) Field of Classification Search
CPC ................ B01L 3/502; B01L 3/50825; B01L 2300/047; B01L 2200/0605; B01L 2300/042; B01L 2400/0406; A61B 5/150351; A61B 5/150022; A61B 5/150343; A61B 5/150267; A61B 5/150251
See application file for complete search history.

(56) References Cited

U.S. PATENT DOCUMENTS

| 4,088,448 A * | 5/1978 | Lilja ...................... B01F 13/00 356/246 |
| 5,674,457 A | 10/1997 | Williamsson et al. |
| 6,333,007 B1 * | 12/2001 | Svensson ............ B01F 11/0266 422/404 |
| 2007/0036684 A1 * | 2/2007 | Burkhardt .......... G01N 35/1016 422/400 |
| 2009/0191643 A1 * | 7/2009 | Boehm ............. B01L 3/502738 436/164 |
| 2014/0275866 A1 * | 9/2014 | Gunnerson ........ A61B 5/14507 600/309 |

FOREIGN PATENT DOCUMENTS

WO WO-2015193194 A1 * 12/2015 ......... G01N 21/6428

OTHER PUBLICATIONS

"Neoteryx: The blood microsampling innovator," Neoteryx Website, Available Online at https://www.neoteryx.com/micro-sampling-capillary-blood-collection-devices, Retrieved on Mar. 5, 2019, 7 pages.

\* cited by examiner

*Primary Examiner* — Matthew D Krcha
*Assistant Examiner* — Sophia Y Lyle
(74) *Attorney, Agent, or Firm* — McCoy Russell LLP (57) ABSTRACT

Methods and systems are provided for a rotating capillary chamber. In one example, a system comprises a rotating capillary chamber arranged in a body of a fluid collection device, wherein the capillary chamber may rotate between two or more positions.

14 Claims, 7 Drawing Sheets

METHODS AND SYSTEMS FOR A CAPILLARY DEVICE

CROSS REFERENCE TO RELATED APPLICATIONS

The present application claims priority to U.S. Provisional Application No. 62/595,999, entitled "METHODS AND SYSTEMS FOR A CAPILLARY DEVICE," and filed on Dec. 7, 2017. The entire contents of the above-listed application are hereby incorporated by reference for all purposes.

FIELD

The present description relates generally to a capillary device comprising a rotating sample collection chamber.

BACKGROUND

Microfluidic samples may be used for a variety of purposes. Frequently, they are used to characterize or detect components or compounds of interest within a sample. When a sample is collected, it is important to collect as pure of a sample as possible as well as to maintain the integrity of the sample after collection. However, fluid samples are prone to a number of points of contamination. For example, during collection substances other than the fluid of interest may be sampled. Once collected, the fluids are prone to spillage, otherwise having undesired contact with handlers, or being otherwise contaminated by their surroundings. It is therefore important to collect fluids in devices that minimize unintentional exposure, contamination, or release of the samples during collection, storage, transportation or manipulation.

Current collection devices use a variety of methods such as lids, in an effort to address some of these issues. However, these devices must be opened to insert and dispense the sample or capillary tubes attached to a reservoir, all of which have drawbacks. For example, some assays require that the collected fluid be immediately combined with another substance. If the collection device contains a pre-filled substance, it must be opened, or a seal otherwise ruptured in order to introduce the collected fluid, increasing the risk of spillage and contamination. Additionally, the amount of fluid collected by a capillary tube is imprecise. Further, a capillary tube may need to be applied multiple times to a fluid source to acquire the desired amount of fluid for the fluid sample, increasing the likelihood of sample contamination.

Other collection devices require venting or the addition of compressed air in order to force the collection mechanism to release the collected fluid into a reservoir, again increasing the likelihood of contamination and possible exposure. There is therefore a need for collection devices that are simple to use and reduce the likelihood of contamination and/or exposure.

SUMMARY

Provided herein is a microfluidic sample collection device and means for fluid collection of microfluidic samples including both environmental and bodily fluid samples. The microfluidic sample collection device described herein can be used to collect any type of liquid or semi-solid desired. In some embodiments, the microfluidic device is designed to collect blood, including human blood. The microfluidic collection device may collect a precise amount of fluid, protect the sample from contamination, and prevent handlers from being exposed to the fluid sample.

The microfluidic sample collection devices as described herein comprise a capillary chamber in a rotatable element. While a disc is used in as an exemplary rotatable element, the rotatable element may be any rotatable shape including, but not limited to, a disc, a cylinder, a sphere, a complex geometrical form, or a rotatable part or section of one of these geometric shapes. The rotatable element is attached to a main body which may be sealed or attached to a receptacle, where the capillary chamber remains parallel to a vertical axis as it rotates or spins about an axis of rotation. In one aspect, the capillary chamber is rotatably arranged within the interior surfaces of the rotatable element. In another example, the entire rotatable element containing the capillary chamber rotates. In this way, a combination of the rotatable element and the main body comprise a fixed profile when rotating the capillary chamber between open and dispense positions. In one aspect, the capillary chamber may rotate about an axis of rotation perpendicular to the rotatable element, where interior surfaces of the rotatable element or the rotatable element holder brush against an opening of the capillary chamber which may be chamfered at its outer edge. In some examples, rotating the rotatable element may create a seal between the capillary chamber and the body. This seal may aid in containment and transport after a sample is collected. In some aspects this seal may also aid in the containment and transport of reagents in the body or receptacle prior to sample collection.

Sample rotatable element rotation can be actuated manually or driven by an external actuator. Rotation methods may be axial or circumferential. In one embodiment, the rotatable element is turned by rotating an axial axle. In another embodiment, the rotatable element is turned by actuating a lever extending from the rotating element.

In some aspects, the rotatable element may have protrusions to assist in actuating the rotation of the rotatable element and/or capillary chamber. For example, the device may have a first protrusion protruding from the center of a first surface of the rotatable element and a second protrusion protruding from a second, different surface of the rotatable element, wherein the second surface may be opposite the first surface in some examples.

In some aspects, the capillary chamber may comprise a single opening, trapping the collected fluid sample within it. The shape of the capillary chamber may be any shape desired. Further, the size of the opening where the sample is to be collected, the volume of the capillary chamber, and the width of the capillary chamber may be independently varied depending on the type and amount of liquid to be collected. While the capillary chamber may be any shape desired, in some embodiments it comprises a triangular cross-section, wherein corners of the triangular cross-section are rounded.

The capillary chamber may be made of any substance generally used, including, but not limited to, thermoplastic and/or organic compounds alone or in combination. In some embodiments, the capillary chamber may be coated with a substance that assists in drawing the fluid within it and/or which forms a reaction mixture required for preservation and/or testing of the sample.

In some aspects, the device may comprise a locking mechanism which prevents the rotatable element and/or capillary collection chamber from rotating. Such a mechanism may be any mechanism useful for such a device. In some embodiments, it may be a hook mechanism. In other embodiments, it may be a step rotation mechanism such as the type found in a zip tie where once it is rotated it cannot be moved in the reverse position. While such mechanisms may be used for a variety of purposes, in some embodiments, such mechanisms may be used to prevent tampering and/or prevent multiple uses of the device.

Generally, the device may rotate between at least two positions. This plurality of positions comprises two or more of a first (open), second (closed), and third (dispensing) positions. At the open position, the device can collect a microfluidic sample of the liquid of interest. The device is then rotated to the closed position at which point the liquid is sealed within the device. In such a position it may be sealed, stored and/or transported. In further embodiments, the device may rotate to a third or dispensing position, expelling the liquid into a receptacle or reservoir which may be empty, or contain one or more substances useful for processing the collected liquid. For example, if blood is collected, the receptacle may further comprise heparin for plasma separation. The device may rotate between an open and closed position, an open and dispense position, or an open, closed and dispense position or any other useful combination. In some embodiments, the device may be limited to rotating between two positions, the open and closed position or the open and dispense position. In other examples, the device may rotate between an open, closed, and dispense position. Such rotation of the device moves the capillary chamber into the appropriate position to receive, seal or dispense the microfluidic sample as determined by the specific position in which the rotating element is placed.

While the device and/or capillary chamber may be made of any suitable material, in some embodiments, they may be made of a transparent polymer such as, but not limited to, polycarbonate, acrylic, and polystyrene. In additional embodiments, some or all of the device, rotating element and/or capillary chamber may comprise an elastomeric material such that fluids, for example a reagent, can be introduced using an implement such as a syringe, without requiring the device to be opened. In other embodiments, reagents may be introduced into a receptacle through the capillary chamber.

In order to collect the microfluidic sample, the capillary chamber may be placed against the sample, drawing in the desired amount of liquid. The capillary chamber is then rotated from the open position to either the closed or dispensing position. In the closed position, liquid is prevented from entering or exiting the device, forming a seal within the rotating element and/or between the rotating element and the main body, and allowing for hermetically sealed storage and transportation, thereby limiting contamination or exposure. When rotated to the third position, the liquid may dispense into a receptacle for storage and/or to undergo a reaction. The dispense position may include rotating the rotatable element such that the opening aligns with a second aperture of the slot, enabling the capillary chamber to fluidly couple to a receptacle or similar device. In some aspects, the capillary chamber may expel liquid into the receptacle with no net pressure change in the chamber when in either the closed position or the dispensing position, thereby obviating the need for venting of these chambers when the sample is introduced.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIGS. 1A through 3B are shown approximately to scale. However, other relative dimensions may be used without departing from the scope of the present disclosure.

DETAILED DESCRIPTION

Figure 3A:
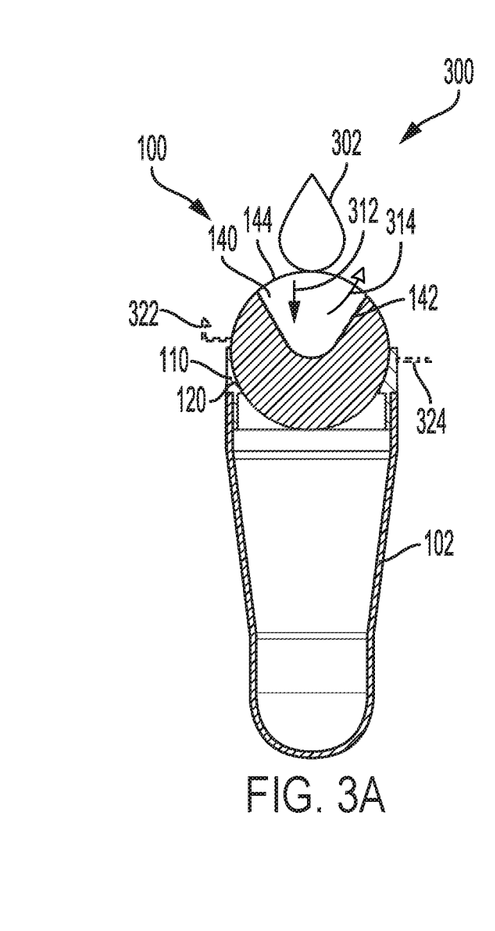
FIG. 3A shows an open position of the device for collecting a fluid sample.
Figure 4:
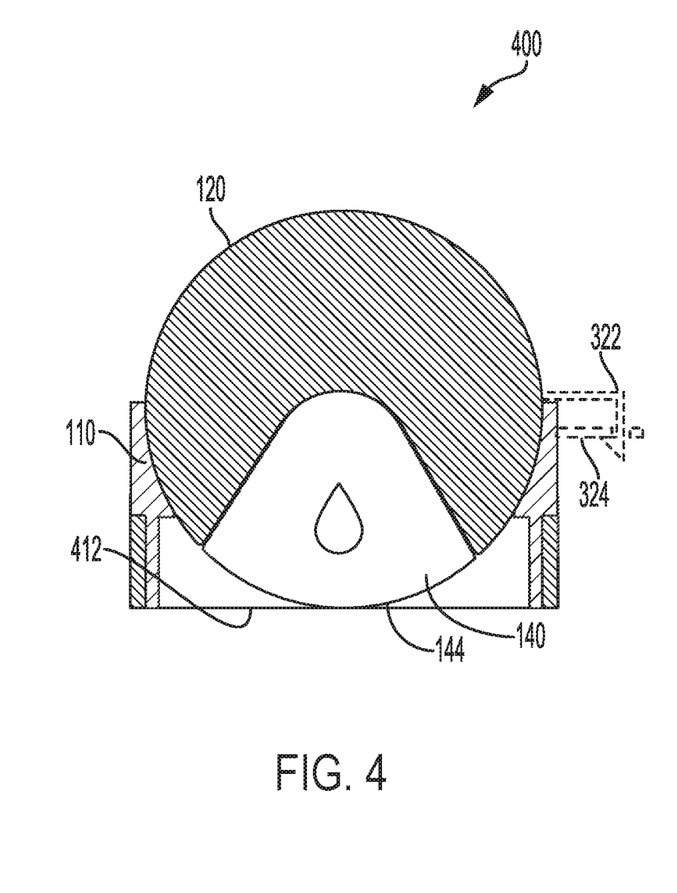
FIG. 4 shows an additional embodiment of the device for collecting a fluid sample.
Figure 5A:
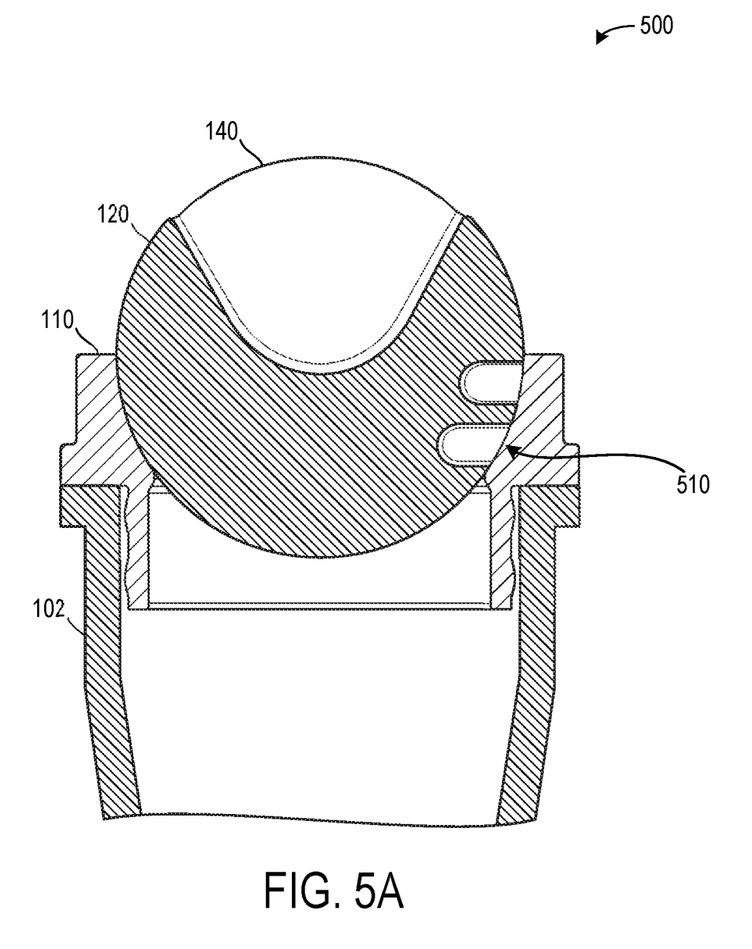
FIGS. 5A and 5B show additional embodiments of the device for introducing a reagent to the fluid sample.
Figure 5B:
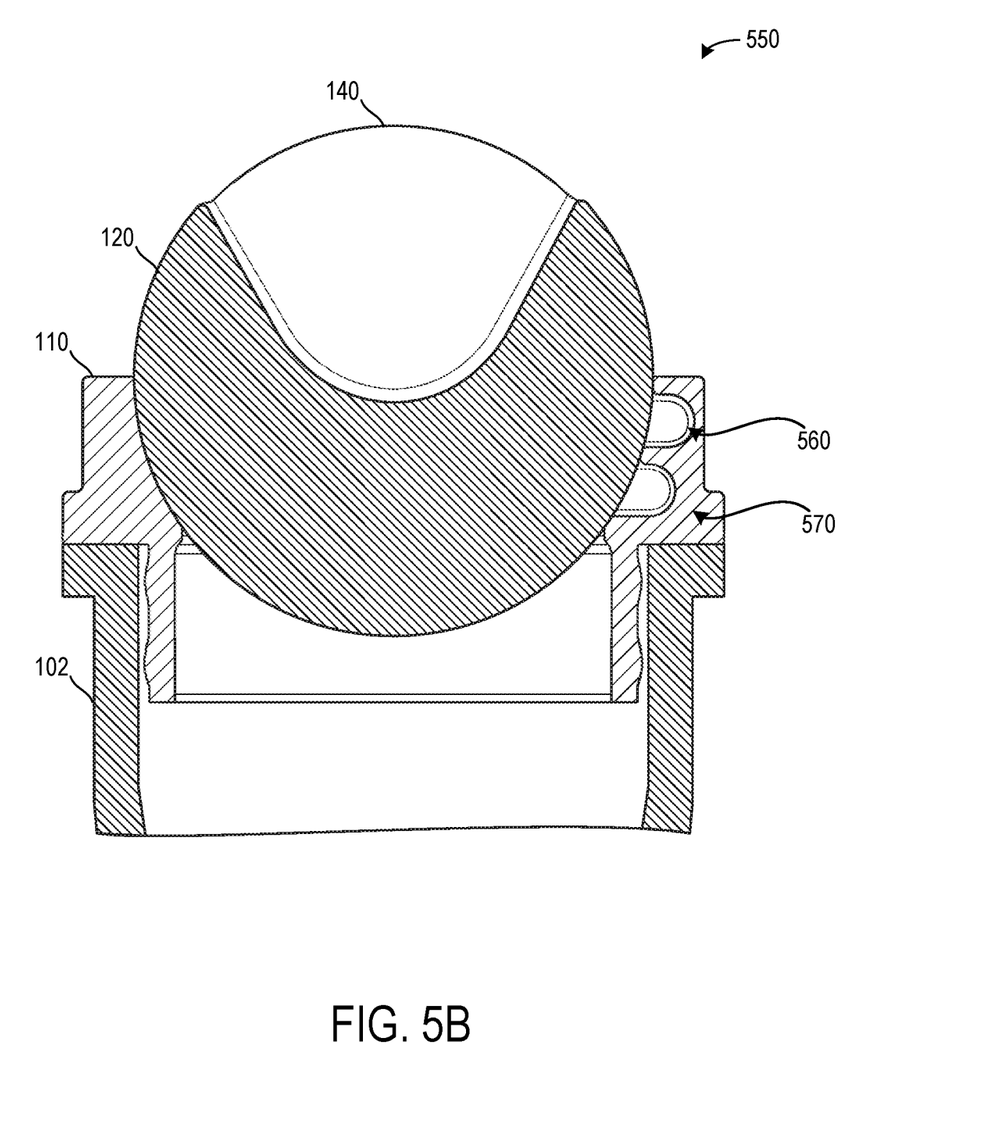
Figure 6:
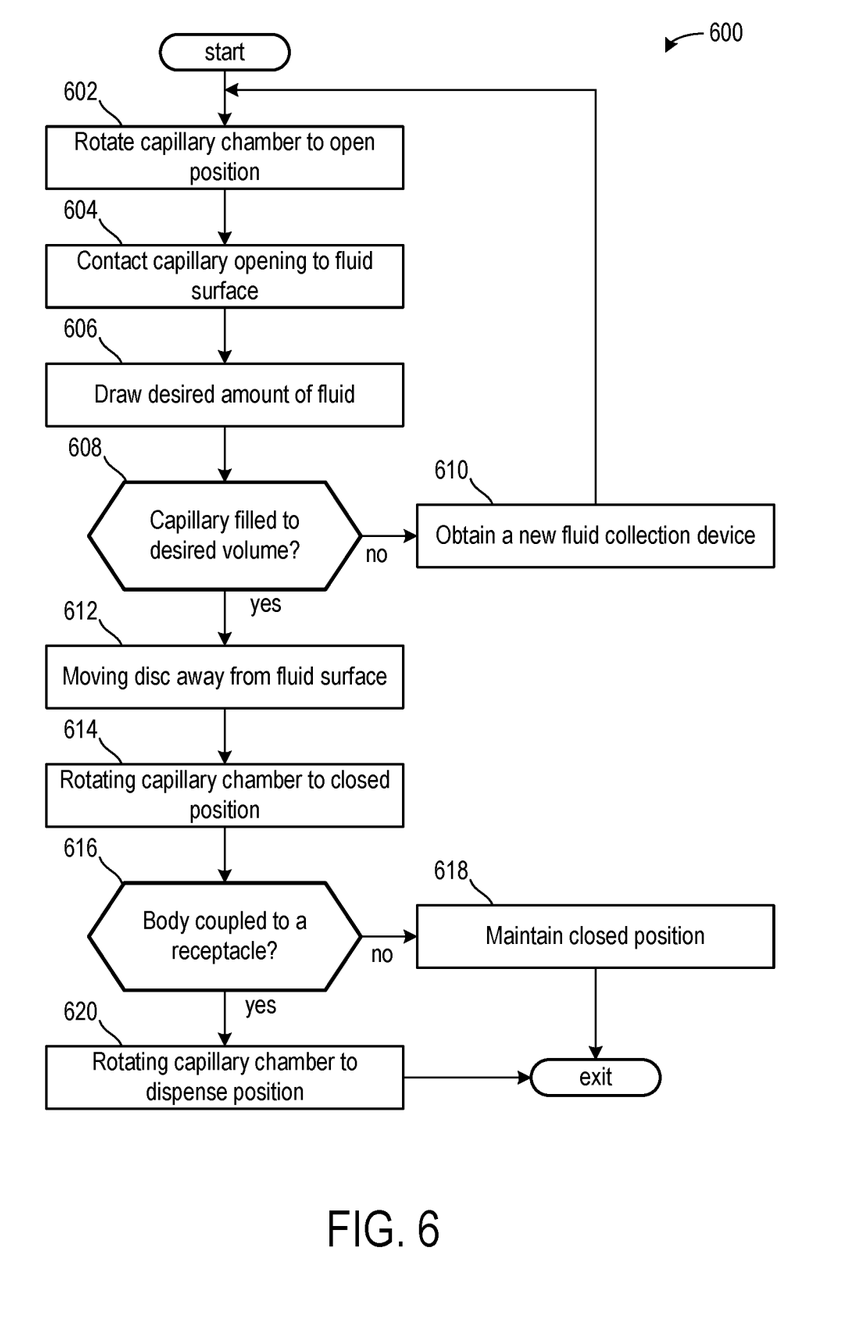
FIG. 6 shows a method for operating the device for collecting a fluid sample.

The following description relates to systems and methods for a device comprising a capillary chamber in a rotatable element. While a disc is used as an exemplary rotatable element, the rotatable element may be any rotatable shape including, but not limited to, a disc, a cylinder, a sphere, a complex geometrical form, or a rotatable part or section of one of these geometric shapes. Various views of the device are illustrated in FIGS. 1A, 1B, 2A, 2B, and 2C. The views depict a main body of the device, wherein there may be a slot for a disc to be rotatably arranged. The disc may comprise a capillary chamber configured to draw a fixed amount of fluid. The capillary chamber may draw fluid in an open position, as shown in FIG. 3A. Alternatively, the capillary chamber may dispense fluid in a dispense position, as shown in FIG. 3C. The capillary chamber may be sealed from an ambient atmosphere and a receptacle in a seal position, shown in FIG. 3B. An embodiment of the device free of the receptacle is shown in FIG. 4. FIGS. 5A and 5B illustrate additional embodiments of the rotatable element and the main body which may optionally comprise recesses for storing a compound separately from a sample collected in the capillary chamber. A method for operating the device to collect a fluid sample is shown in FIG. 6.

FIGS. 1A-4 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example. It will be appreciated that one or more components referred to as being "substantially similar and/or identical" differ from one another according to manufacturing tolerances (e.g., within 1-5% deviation).

Figure 1A:
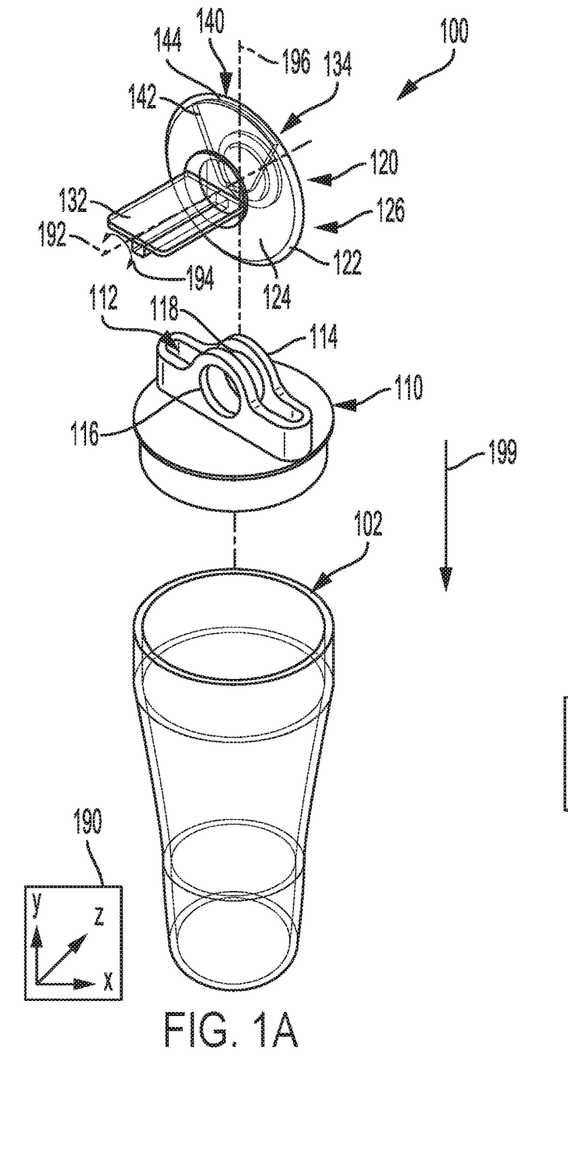
FIG. 1A shows an exploded view of a device for collecting a fluid sample.

Turning now to FIG. 1A, it shows an exploded view of a device 100. The device 100 may comprise a disc 120 and a main body 110. The device 100 may further include or be designed to attach to a receptacle 102 which may be in sealing contact with the main body 110.

In one example, the device 100 is a microfluidic collection device. The fluid may be a variety of fluids, including but not limited to liquids with organic and inorganic components including, but not limited to, environmental liquids such as water, or bodily liquids including, but not limited to, blood, gingival crevicular fluid, serum, plasma, urine, nasal swab, cerebrospinal fluid, pleural fluid, synovial fluid, peritoneal fluid, amniotic fluid, gastric fluid, lymph fluid, interstitial fluid, tissue homogenate, cell extracts, saliva, sputum, stool, physiological secretions, tears, mucus, sweat, milk, semen, seminal fluid, vaginal secretions, fluid from ulcers and other surface eruptions, blisters, and abscesses, and extracts of tissues including biopsies of normal, and suspect tissues or any other constituents of the body which may contain the target substrate of interest. Such bodily fluids may be collected from any animal, including humans. In one example, the fluid is blood, including human blood.

An axis system 190 is shown comprising three axes, namely an x-axis parallel to a horizontal direction, a y-axis parallel to a vertical direction, and a z-axis perpendicular to each of the x- and y-axes. An axis of rotation 192 is shown extending in a direction parallel to the z-axis. A vertical axis 196 is shown extending along the y-axis perpendicular to the axis of rotation 192. A direction of gravity 199 (herein, gravity 199) is shown parallel to the vertical axis 196.

The disc 120 may comprise a thermoplastic and/or organic compound. In one example, the disc 120 comprises styrene, polycarbonate or acrylic, or a combination thereof. For example, the disc 120 may comprise polystyrene, polyether ether ketone, polyethylene terephthalate, polymethylmethacrylate, cyclic olefin copolymer, polyetherimide, polydimethylsiloxane, glass, silicon or other thermoplastic or organic compounds alone or in combination. Additionally or alternatively, the compounds forming the disc such as polystyrene and the polycarbonate may be substituted with one or more functional groups, including but not limited to halogens, heteroatoms, ketones, aldehydes, carbon chains, and the like. It will be appreciated that the disc 120 may comprise other materials comprising properties similar to those listed above, including, but not limited to, similar strength, opacity, hardness, rigidity, friction, ductility, impact strength, able to maintain appropriate tolerances, have high surface energy (conducive to capillary action) and structurally tough. In one embodiment, some or all of the disc 120 is coated with a surfactant to aid in sample collection. In another embodiment, some or all of the disc 120 is coated with dried reagent that interacts with the sample (for example, heparin to prevent coagulation).

The main body 110 may comprise a plastic. In one example, the main body comprises polyethylene. However, it will be appreciated that the main body 110 may comprise other materials comprising similar properties (e.g., similar strength, opacity, hardness, rigidity, friction, ductility, and impact strength) to that of polyethylene PE. For example, the main body 110 may additionally or alternatively comprise other hydrocarbon polymers. Some hydrocarbon polymers may have lubricious, ductile properties, such as, for example, but not limited to, polypropylene (PP), nylon 6, nylon 6/6, nylon 12, polyamide, polyvinylchloride PVC, polyvinyl acetate PVA or Polytetrafluoroethylene PTFE.

The disc 120 may comprise an outer edge 122 arranged between a front surface 124 and a back surface 126. The disc 120 may be hollow and its volume defined by the outer edge 122, the front surface 124, and the back surface 126. Additionally or alternatively, interior portions of the disc 120 may be solid. The hollowness and/or solid portions of the interior of the disc 120 may be varied, allowing for alterations in the volume of free space and/or sample storage to change based on the particular type of sample or the amount of sample to be collected.

Each of the outer edge 122, front surface 124, and the back surface 126 may be smooth and flat. The outer edge 122 may be curved. In one example, the outer edge 122 does not comprise a corner. As such, the disc 120 may comprise an arc-shaped outer edge 122 arranged between and physically coupled to each of the front surface 124 and the back surface 126.

The disc 120 may be disc-shaped. A cross-section of the disc 120 taken in a plane parallel to an x-y plane may be substantially circular with a diameter of the disc 120 being defined by the outer edge 122. As such, the outer edge 122 may be ring-shaped and the front 124 and back 126 surfaces may be identical circles. In this way, the combination of the front surface 124, the back surface 126, and the outer edge 122 may define a shape of the disc 120. That is to say, the outer edge 122, the front surface 124, and the back surface 126 may be a single, continuous piece generating a shape of the disc 120.

The front surface 124 and the back surface 126 may be substantially identical in size, shape, and smoothness. However, in some embodiments the front surface 124 and the back surface 126 may further comprise a protrusion. The protrusions may be the same or different and serve the same, substantially similar or different functions. For example, in some embodiments, the front surface 124 may comprise a first protrusion 132 and the back surface 126 may comprise a second protrusion 134. In some embodiments, the protrusions may provide a means for rotating the disc 120 and or attaching it to the main body 110. While a first protrusion 132 is shown on the front surface 124 and a second protrusion 134 is shown on the back surface 126, the size and appearance of the first and second protrusions 132 and 134 may be interchangeable. That is, the component described as the first protrusion 132 may be attached to either the back surface 126 or the front surface 124 or both. Similarly, the second protrusion 134 may be attached to the front surface 124 or the back surface 126, or both.

The first protrusion 132 and the second protrusion 134 may be different in size, shape, and function. In some examples, the first protrusion 132 and the second protrusion 134 may be substantially similar in size, shape, and function. In one example, the first protrusion 132 is bigger than the second protrusion 134. As such, the first protrusion 132 and second protrusion 134 are the only components of the front 124 and back 126 surfaces, respectively, which are not flush with the surfaces, thereby disrupting a smoothness of the front surface 124 and back surface 126.

The second protrusion 134 may be smaller than the first protrusion 132 and may be fixed to the back surface 126. In one example, both the second protrusion 134 and the back surface 126 are fixed and immovable relative to each other. The second protrusion 134 may comprise a cylinder shape and a circularly shaped cross section.

The first protrusion 132 may be physically coupled to the front surface 124. In some aspects, the first protrusion 132 may be configured to actuate or rotate the disc 120. In one example, actuating may include spinning. In some examples, the disc may rotate proportionally to the first protrusion 132. For example, if the first protrusion 132 is rotated 90 degrees, then the disc 120 is also rotated 90 degrees. It will be appreciated that the rotation may be disproportional such that the disc 120 rotates more or less than the first protrusion 132. By rotating the disc 120 via the first protrusion 132, a position of a chamber 140 may be adjusted, as will be described below.

Although the first protrusion 132 is depicted as having a T-shape in the embodiment in FIG. 1A, it will be appreciated that the size and shape of the first protrusion 132 may be adjusted without departing from the scope of the present disclosure. For example, a length of the first protrusion 132 may be reduced to decrease an overall size of the disc 120. Additionally or alternatively, the first protrusion 132 may protrude inwardly into a body of the disc 120 such that a device (e.g., a coin, screwdriver, hex key, or the like) may be used to engage with the first protrusion 132 to rotate the chamber 140. Additionally or alternatively, the first protrusion 132 may be omitted from the disc 120, wherein the chamber 140 may be rotated by other means (e.g. external driver or electronically actuated via a controller). In one example, the controller may be user activated. In another example, an RFID tag (or the like) can be used. In a further example, the device may automatically rotate or spin the disc once a sample is collected.

Additionally or alternatively, the chamber 140 may be rotated in response to an external force applied to the disc 120. For example, the chamber 140 may be rotated to one of three positions, including a first position, a second position, and a third position which may be separated from each other by equal or varying amounts. In one example, the first position is separated from the second position by 90 degrees. Similarly, the second position is separated from the third position by 90 degrees. As such, the first position may be separated from the third position by 180 degrees. In this way, the second position is between the first and third positions.

In some examples, the disc 120 may comprise threading or the like on its outer edge 122 which may allow the capillary chamber 140 to rotate in a stepwise manner. That is to say, threading and/or ridges arranged along some portion of the outer edge 122 may contact complementary threading and/or ridges on interior surfaces of the main body 110 such that the disc 120, and therefore capillary chamber 140, rotate incrementally. In other examples, the disc 120 may move with minimal amounts of friction. In some examples, the disc 120 may only move in one direction. That is, once a sample enters the capillary chamber 140, the disc 120 may only rotate to the closed and/or dispensing position, it may not open again. In other examples, the disc 120 may rotate freely in either direction.

The capillary chamber 140 may rotate from the first position to the second position in response to any means generally used. In some embodiments, the chamber 140 may rotate in response to a pressure applied to the disc 120 from a first direction. The pressure may be applied directly to the disc, or indirectly through actuation of the first protrusion 132.

The first direction may be a direction parallel to the positive y-axis. In the second position, the chamber 140 may be rotated to the third position in response to a pressured applied in the first direction, As such, the chamber 140 may rotate in a similar direction each time a pressure is applied to the disc 120 in the first direction until the chamber 140 reaches the third position. In the third position, the chamber 140 may no longer rotate in response to a pressure being applied to the disc 120 in the first direction. If a pressure is applied to the disc 120 in a second direction, opposite the first direction, then the chamber 140 may rotate from the third position to the second position or from the second position to the first position.

In some embodiments, rotation of the disc including the capillary chamber 140 may comprise only two positions. For example, the capillary chamber 140 may be rotated between an open position and a closed position, wherein the open position may be configured to receive a fluid sample and dispense a fluid sample. When rotated to the closed position, the capillary chamber 140 is prevented from expelling the fluid sample. In the closed position, the opening 144 faces an interior surface of the main body 110 and may be hermetically sealed from an ambient atmosphere and the receptacle 102. As another example, additionally or alternatively, the capillary chamber 140 may be rotated between an open position and a dispense position such that it may either receive or expel a liquid such as the microfluidic sample, a reagent, or a combination of a reagent and the microfluidic sample.

The chamber 140 may be arranged within interior surfaces of the outer edge 122, the front surface 124, and the back surface 126. While the capillary chamber 140 may be any shape generally used, in some embodiments, the capillary chamber is V-shaped. In one example, the V-shape is rounded and not pointed at the bottom of the V. Additionally or alternatively, the capillary chamber may be U-shaped, C-shape, or other similar curved shaped. In one example, a cross-section of the capillary chamber taken along the vertical axis 196 is substantially triangular, wherein corners of the triangle are rounded. Furthermore, the capillary chamber 140 may comprise a perimeter wall 142, which defines both a volume and a boundary of the capillary chamber 140 within an interior of the disc 120. Between extreme ends of the perimeter wall 142, the capillary chamber 140 comprises an opening 144.

In one example, the chamber 140 is a cutout arranged in the disc 120. That is to say, the disc 120 may be a solid disc comprising the chamber 140, where the chamber 140 may be the only hollow portion of the disc 120. The chamber 140 may rotate as the disc 120 rotates due to actuation of the first protrusion 132 or other rotating mechanism described above. The chamber 140 may be shaped to perform a capillary action when in contact with a fluid.

The opening 144 may comprise one or more features for aiding in collection of a fluid sample. For example, the opening 144 may be chamfered to both increase a capillary action when in contact with a surface of a fluid and to prevent inadvertent leaks and/or spills from the capillary chamber 140. In some examples, the perimeter walls of the capillary chamber may be angled about 45 degrees and extend about 0.25 mm. A thickness of the capillary chamber 140 (e.g., its distance between the front 124 and back 126 surfaces) may be between 0.1 to 2.0 mm. Thus, the opening 144 may be the thinnest portion of the capillary chamber 140. The distance between the two walls may be uniform or have regular or irregular spacing. For example, the distance between the two walls may be tapered or the spacing may form a pattern. In some examples, the spacing and shape of the distance between the front and back surfaces may be determined based on the desired capillary action to draw the sample of interest into the capillary chamber.

When the opening 144 faces a direction opposite the direction of gravity 199, the capillary chamber 140 is in the first position. Herein, the first position is referred to as the open position. In the open position, the capillary chamber 140 may draw a sample through its opening 144 when the opening 144 is put in contact with a surface of a fluid. For example, when the opening 144 is put in contact with a drop of blood, some or all of the drop of blood may flow through the opening 144 and into the capillary chamber 140. A volume of fluid is drawn into the capillary chamber 140, wherein the volume may be substantially equal to a volume of the capillary chamber 140 below the chamfer. The volume of the capillary chamber may be between 1 pL to 100 microliters (μL). While the volume of the capillary chamber limits the total volume that may be drawn into the chamber, the actual volume drawn in may be regulated by various properties of the disc, the capillary chamber, reagents present on or in the capillary chamber, the material properties of the disc and/or capillary chamber, or a combination thereof.

For example, if the volume of the capillary chamber 140 is 10 μL, then once the opening 144 of the capillary chamber 140 contacts a surface of a fluid sample, 10 μL of fluid may be drawn into the capillary chamber 140. In one example, the capillary chamber receives 10 μL of fluid upon touching the fluid once. While the liquid is drawn in using capillary action, the surface of the capillary chamber may be constructed of or coated with substances that assist in drawing the desired sample into the chamber. In some examples, the surface of the capillary chamber may be constructed of or coated with substances that assist in drawing the desired amount of a sample into the chamber. In some aspects, this may be due to a coating applied to interior surfaces of the disc 120 and/or capillary chamber 140, including but not limited to, a surfactant, thereby decreasing a surface tension between surfaces of the capillary chamber 140 and the fluid. In other aspects, the chamber may be formed of a material which has high surface energy and wetting properties to assist in drawing the fluid into the chamber.

When the opening 144 faces the same direction as gravity 199, the capillary chamber 140 is in the third position. Herein, the third position is referred to as the dispense position. In the dispense position, the capillary chamber 140 may expel any fluid arranged therein in response to either internal forces (e.g. capillary forces acting differently on the sample vs a reagent) or an external stimulus (e.g. gravity). Tapping, shaking, mechanical vibration, oriented electromagnetic fields, pressure and/or other external forces (e.g. wicking) can assist fluid extraction from the capillary chamber. The capillary space may also empty when in direct contact with the liquid reagent due to interactions between the sample and reagent.

When the opening 144 is perpendicular to gravity 199, the capillary chamber 140 is in the second position. Herein, the second position is referred to as the closed position. In the closed position, the opening 144 faces an interior surface of the main body 110 and may be hermetically sealed from an ambient atmosphere and the receptacle 102. In one example, the capillary chamber 140 is rotated to the closed position when it is desired to transport the fluid sample. In some embodiments, the main body 110 may have a locking mechanism, preventing the disc 120 from rotating from the desired first, second, or third position. The main body 110 and the arrangement of the disc 120 into the main body 110 is described in greater detail below.

In some embodiments, the disc 120 may be a hollow or partially hollow disc, wherein the chamber 140 is arranged within interior surfaces of the disc. The first protrusion 132 may be configured to rotate the chamber 140 within the interior surfaces of the disc 120 such that only the chamber 140 rotates and the disc 120 does not. As such, the disc 120 may comprise first and second openings arranged opposite to one another, wherein the capillary chamber 140 may fluidly couple to a first opening in a first position and to a second opening in a second position. The first position may correspond to a position where the capillary chamber 140 may be positioned to receive and/or draw fluid (e.g., draw a sample). The second position may correspond to a position where the capillary chamber 140 may be positioned to dispense a fluid and/or a sample into the receptacle 102. There may be a plurality of positions between the first and second positions wherein the capillary chamber may be sealed from each of an ambient atmosphere and the receptacle 102.

In other embodiments, the first protrusion 132 may be configured to rotate the disc containing the chamber 140 such that the entire disc rotates. In some aspects, such as when the chamber 140 rotates within the disc, the disc may further comprise openings angled to or diametrically opposed to one another, where the opening 144 of the chamber 140 may align with the openings in the first and third positions.

The main body 110 comprises a slot 112 traversing the main body 110 along the y-axis. The slot 112 may traverse all or part of the main body 110 in a direction parallel to the gravity 199. In one example, the slot 112 is completely open. As such, the slot 112 may fluidly couple an environment above the main body 110 to an environment below the main body 110. In some embodiments, the opening of the slot 112 may directly correspond to the opening of the capillary chamber 140. A length of the slot 112 may be equal to between 40-95% of the diameter of the main body 110. In one example, the length of the slot 112 is equal to exactly 80% of the diameter of the main body 110. Additionally or alternatively, the length of the slot 112 may correspond to a diameter of the disc 120 such that the disc 120 may be arranged within the slot 112.

While the main body 110 may be any shape desired, generally it is of a shape suitable for attachment to a tube, cuvette, or other reservoir for depositing the fluid sample. In some examples, the main body 110 may be cylindrical and comprise a circular cross-section. The slot 112 may comprise a rectangular prism shape with a rectangular cross-section, wherein corners of the rectangular cross-section are rounded. In some embodiments, the slot 112 may be shaped similarly to the disc 120, wherein the slot 112 functions as a housing for the disc 120 to rotate within.

A header 114 may be arranged around an upper portion of the slot 112 and physically coupled to a top surface of the main body 110. In some examples, the header 114 may function as an extension of the slot 112. Furthermore, the header 114 may comprise a first through-hole 116 and a second through-hole 118.

Figure 1B:
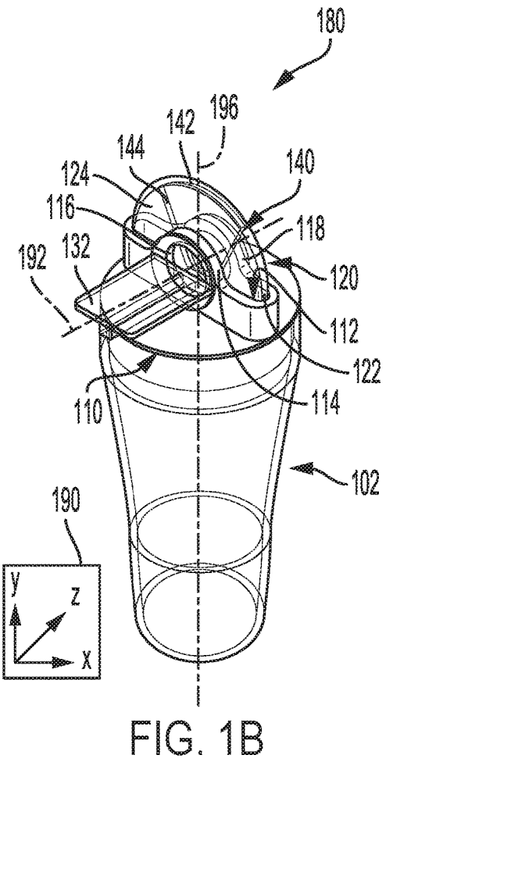
FIG. 1B shows a perspective view of the device in an assembled embodiment.

The disc 120 may be arranged within the slot 112 of the main body 110 as shown in the embodiment of FIG. 1B. In some examples, the disc 120 may not be removable from the slot 112 when the first protrusion 132 extends through the first through-hole 116 and when the second protrusion 134 extends through the second through-hole 118. However, when inserted through the first through-hole 116, the first protrusion 132 may still be configured to rotate the disc 120, and therefore the capillary chamber 140, within the slot 112.

In some embodiments, the disc 120 and the main body 110 may be produced as a single piece. That is to say, the disc 120 and the main body 110 may be formed via a mold, wherein the first protrusion 132 and the second protrusion 134 extend through the first through-hole 116 and the second through-hole 118, respectively.

In some embodiments, the main body 110 may form an enclosed chamber such that rotation of the disc 120 deposits the collected fluid within the main body 110 as described in further detail with respect to FIG. 4. In other embodiments, such as when rotated to the closed position, the main body 110 may trap the fluid in the capillary chamber. In further embodiments, the main body 110 may be attached to a receptacle 102. The receptacle 102 may comprise any useful size or shape. For example, it may be a vial, tube, cuvette, or other shape of reservoir. In some aspects, the receptacle 102 may hermetically seal with the main body 110 such that an inner contents of the receptacle 102 are fluidly sealed from ambient atmosphere. The contents of the receptacle 102 or a sealed main body 110 may be referred to interchangeably such that substances within the receptacle 102 may additionally and/or alternatively be found in a sealed main body 110.

The receptacle 102 may be empty or may comprise one or more compounds capable of reacting with the fluid sample based on a sample test type and/or the sample type. For example, the capillary chamber 140 may comprise one or more of a clot activator, gel for serum separation, lithium heparin and a gel for plasma separation. In some embodiments, the capillary chamber 140 may comprise a clot activator and the receptacle may comprise a gel for serum separation.

Additionally or alternatively, in some embodiments, the capillary chamber 140 and/or the receptacle 102 may be uncoated or may comprise and/or be coated with one or more of a plastic serum, $K_2EDTA$, a thrombin-based clot activator, a thrombin-based clot activator with gel for serum separation, glass, plastic, sodium heparin, lithium heparin, potassium oxalate, sodium fluoride, $Na_2EDTA$, sodium polyanethol sulfonate (SPS), acid citrate dextrose additives (ACD), liquid $K_3EDTA$, spray-coated $K_2EDTA$, buffered sodium citrate, citrate, theophylline, or adenosine, dipyridamole. In another example, if blood is being collected, the receptacle 102 may comprise a clot activator and gel for serum separation. Additionally or alternatively, the receptacle 102 may comprise lithium heparin and a gel for plasma separation. Such additives in the capillary chamber 140 or the receptacle 102 may be in liquid or powder form. For example, the receptacle may contain a first solution comprising trisodium, citric acid, and dextrose in concentrations of 22.0 g/L, 8.0 g/L. 24.5 g/L, respectively or a second solution comprising trisodium, citric acid, and dextrose in concentrations in concentrations of 13.2 g/L, 4.8 g/L, and 14.7 g/L, respectively, or both. In some examples, the receptacle 102 may comprise a filter paper or other similar porous device for collecting the fluid sample.

In some embodiments, the reagents may be arranged in the receptacle 102 during a manufacturing process. Additionally or alternatively, reagents may coat one or more surfaces of the receptacle 102 and/or the capillary chamber 140. The reagents may be present as solids and/or liquids in the form of one or more of powders, gels, films, droplets, and the like. Additionally or alternatively, the receptacle 102 may be sealed with the main body 110, where the main body 110 retains the disc 120. As such, the capillary chamber 140 of the disc 120 may be used to introduce one or more reagents to the receptacle 102. In some embodiments, additionally or alternatively, some or all of the disc 120 and/or the main body 110 may comprise an elastomeric material such that reagents may be added to the receptacle 102 through the elastomeric material. For example, a syringe may press through the elastomeric material and inject a reagent into the receptacle 102.

In some embodiments, additionally or alternatively, the compounds for reacting with the fluid may be arranged in the capillary chamber 140. As an example, the capillary chamber 140 may perform a first reaction with the fluid sample producing a first fluid sample product. The first fluid sample product may be dispensed into the receptacle 102 or other container, where the first fluid sample product may undergo a second reaction or lie dormant. In some embodiments, the capillary chamber 140 may be coated with a powder, gel, film, or other substance capable of reacting with the liquid sample to form the desired reaction.

Figure 2A:
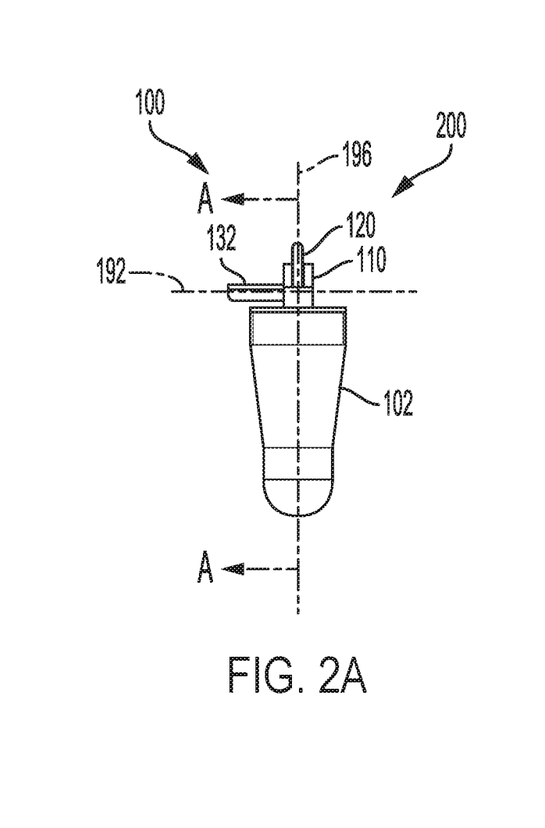
FIG. 2A shows a side-on view of the device for collecting a fluid sample.

FIG. 2A shows a side profile view 200 of device 100 being in an assembled embodiment, such as the embodiment 180 of FIG. 1B. As such, components previously introduced may be similarly numbered in the subsequent figures.

As shown in the side-on view, the first protrusion 132 extends beyond a profile of the receptacle 102 in a direction parallel to the axis of rotation 192 such that a user may more easily actuate the first protrusion about the axis of rotation 192. In some examples, the first protrusion 132 may extend in a direction angled to the axis of rotation. In one example, the first protrusion 132 extends away from the receptacle 102 at an angle 45 degrees to the axis of rotation 192.

In the view 200, the disc 120 may remain in-line with the vertical axis 196 as the disc 120 is rotated about the axis of rotation 192. That is to say, as the capillary chamber (e.g., capillary chamber 140 of FIG. 1A) is moved through the open, closed, and dispense positions, the disc 120 may remain in-line with the vertical axis 196.

Figure 2B:
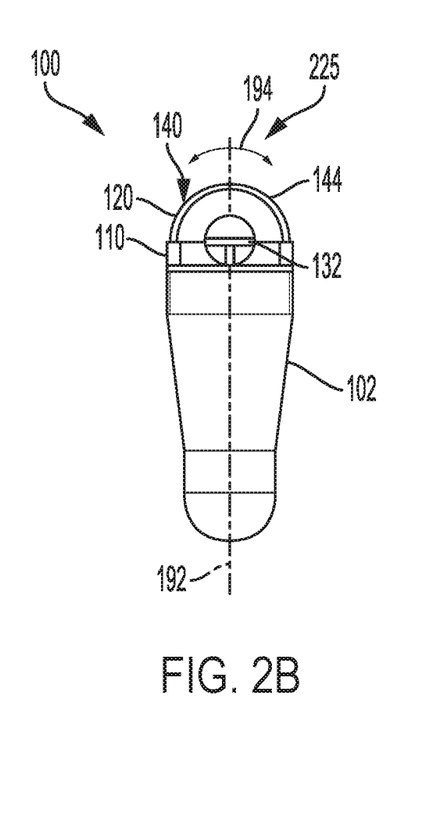
FIG. 2B shows a cross-sectional view according to the cutting plane A-A of FIG. 2A.

FIG. 2B shows a face-on view 225 of the device 100 in the assembled embodiment, wherein the face-on view is taken along the plane A-A of FIG. 2A. The double-headed arrow 194 illustrates the directions about which the disc 120 may rotate. As described above, the capillary chamber 140 may only rotate within a single plane (e.g., the capillary plane). The capillary plane may be a plane perpendicular to the axis of rotation (e.g., axis of rotation 192). As such, the capillary chamber 140 is always parallel to the vertical axis 196, in one example.

Figure 2C:
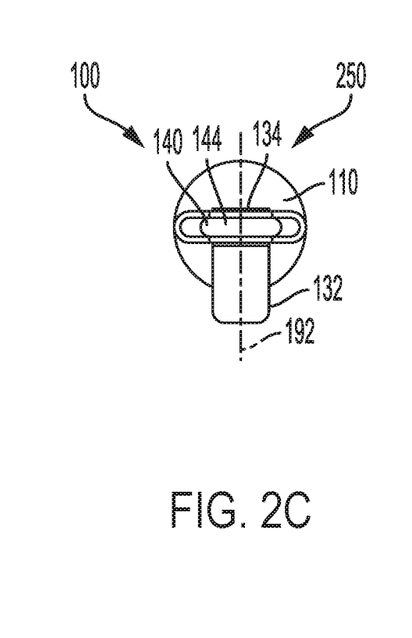
FIG. 2C shows a top-down view of the device for collecting a fluid sample.

FIG. 2C shows a top-down view 250 of the device 100. In the top-down view, the opening 144 is shown. In one example, the device 100 is shown in the open position, wherein the opening 144 faces a direction away from both the receptacle 102 and inner surfaces of the slot (e.g., slot 112 of FIG. 1A).

In some examples, a length of the first protrusion 132 may be greater than a length of the second protrusion 134 and a radius of the main body 110. In some examples, the length of the first protrusion may be between 1.2 to 2 times greater than a radius of the main body 110. In some examples, the length of the first protrusion may be between 1.4 to 1.6 times greater than a radius of the main body 110. In one example, the length of the first protrusion is exactly 1.5 times greater than the radius of the main body 110. Not shown is a lever arm attached to the circumference of the disc that can be moved thru an arc to achieve the same result.

Figure 3B:
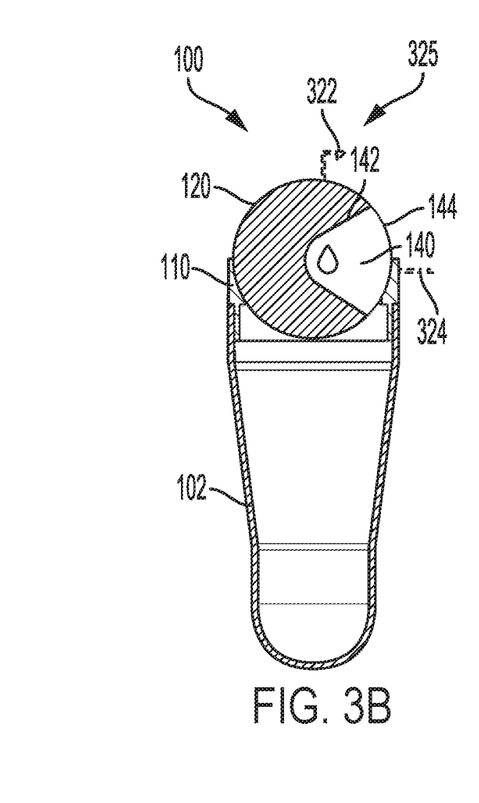
FIG. 3B shows a closed position of the device for collecting a fluid sample.
Figure 3C:
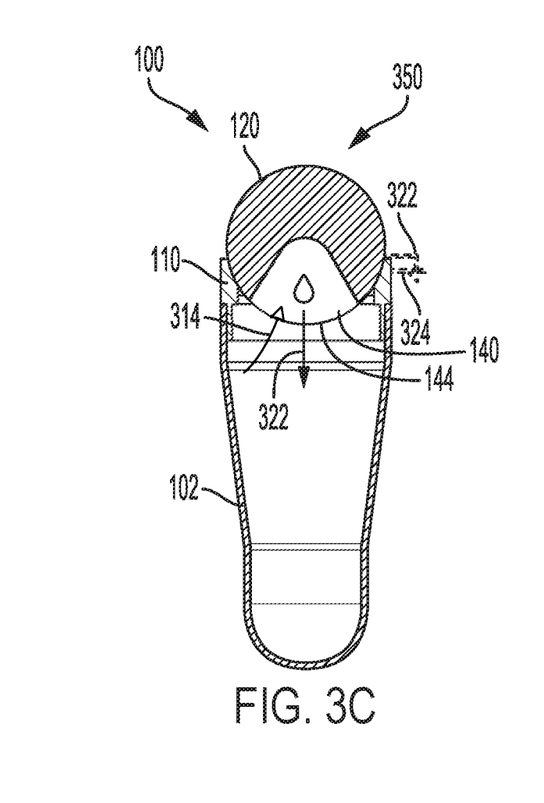
FIG. 3C shows a dispense position of the device for collecting a fluid sample.

Turning now to FIGS. 3A, 3B, and 3C, they show embodiments 300, 325, and 350, respectively, illustrating a progression of the rotation of the disc 120 within the microfluidic collection device 100. Specifically, FIG. 3A shows the device 100 in the open position where the opening 144 of the capillary chamber 140 contacts a surface of a fluid source 302. Arrow 312 represents a flow direction of the fluid sample and arrow 314 represents a flow direction of the displaced air. Herein, arrow 312 may be referred to as fluid sample 312 and arrow 314 may be referred to as air 314. As the fluid sample 312 enters the capillary chamber 140, air 314 may flow out of the capillary chamber. In one example, the fluid sample 312 enters the capillary chamber 140 via the opening 144 and air 314 flows out of the capillary chamber 140 via the opening 144 simultaneously. A shape of the perimeter wall 142 may promote the self-venting (e.g., the escape of air as the fluid sample enters the capillary chamber). Specifically, the curvature of the perimeter wall 142 may allow the incoming fluid sample 312 to force air 314 out of the capillary chamber.

The device 100 is further shown with an optional locking mechanism. While the locking mechanism may have any configuration generally used, in some embodiments the locking mechanism comprises a hook 322 and a receiver 324. The hook 322 may mate with an opening of the receiver 324 such that the disc 120 may no longer rotate. In some examples, the locking between the hook 322 and the receiver 324 may not be released without degrading the locking mechanism (e.g., cracking, snapping, or the like), providing a tamper resistant mechanism to ensure the integrity of the collected sample.

FIG. 3B shows the device 100 in the closed position where the opening 144 may face interior surfaces of the main body 110. The engagement between the opening 144 and the interior surfaces of the main body 110 may prevent fluid from leaving the capillary chamber 140 and air from entering the capillary chamber 140. The hook 322 may be spaced away from the receiver 324 when the device 100 is in the closed position such that the device 100 is not locked. In other embodiments, the device may be capable of locking in the closed position.

As the disc 120 rotates from the open position of FIG. 3A to the closed position of FIG. 3B, interior surfaces of the main body 110 may wipe the opening 144 of the capillary chamber 140 of any residual fluids that did not enter the capillary chamber. As such, an operator using the device 100 may not come into contact with the residual fluids.

FIG. 3C shows the device in the dispense position where the opening 144 of the capillary chamber 140 may allow the fluid arranged therein to flow into the receptacle 102. Specifically, the opening 144 is facing away from the interior surfaces of the main body 110, toward the receptacle 102. The fluid sample 312 may be deposited into the receptacle 102 in response to one or more of tapping the device 100 and/or a fluid in the receptacle coming into contact with the opening 144. As the fluid sample 312 leaves the capillary chamber 140, air 314 may enter the chamber maintaining the interior pressure and obviating the need for external venting/pressure equalization.

Additionally, in the dispensing position, the lock 322 is mated with the receiver 324, such that that disc 120 may no longer be rotated. As described above, this may ensure that the fluid sample 312 in the receptacle 102 may not be modified prior to being characterized at a laboratory.

Turning now to FIG. 4, it shows an embodiment of a device 400, which may be used similarly to the device 100 of FIGS. 1A-3C, except that the device 400 is free of the receptacle 102. The main body 110 may be sealed. In one example, the main body 110 is completely sealed such that the opening 144 is the only opening of the device 400.

In the example of FIG. 4, the device 400 may retain the fluid sample within the capillary chamber while in a position similar to the dispense position shown in FIG. 3C. This may be due to a surface of the main body 110 pressing against the opening 144, thereby sealing the fluid sample in the capillary chamber. Additionally or alternatively, the main body 110 may comprise an interior volume shaped to receive the fluid sample when the device 400 is in the position shown in FIG. 4. In some examples, a lower surface 412 of the main body 110 may be punctured, opened, and/or removed when the main body 110 is coupled to a receptacle 102 or other fluid receiving device. In some aspects, the main body 100 may contain in whole or in part an elastomeric substance allowing the sample to be withdrawn using a syringe. Additionally or alternatively, the lower surface 412 may not be punctured, and a position of the device 400 used to draw the fluid sample into the capillary chamber 140 (e.g., the open position of FIG. 3A) may also be used to dispense the fluid sample to an external fluid receiving device. In this way, the device 400 may seal the capillary chamber 140 for positions outside of the open position. The device 400 may be more compact than the device 100 and therefore more easily transported, while still providing the same capillary action and sealing capacity.

Turning now to FIG. 5A, it shows an embodiment 500 of the device 100 comprising the main body 110, the rotatable element (e.g., disc 120), and the capillary chamber 140. As shown in FIG. 5A, the disc 120 may be further comprise one or more recesses or chambers 510 shaped to hold one or more substances useful for processing the collected liquid including, but not limited to, a reagent, enzyme, anti-coagulant, and the like. The recesses 510 may be fluidly separated from the capillary chamber 140. In this way, compounds in the capillary chamber 140 may be held separately from the substances in the recesses 510 until such a time as mixture is desired. Further, this separation allows for the production of a device pre-loaded with one or more substances useful in analyzing a sample. In some examples, the disc may rotate in a single direction, keeping substances in the recesses 510 in a sealed compartment(s) separate from the sample and/or exposure to the atmosphere until such a time as the substances are combined with the sample.

The recesses 510 may be shaped similarly or differently than the capillary chamber 510 and may contain the same or different substances in dry, powdered or liquid form. A substance may be deposited in one or more of the recesses 510 manually or via capillary action. In some aspects, the substances may be pre-loaded into the recesses 510. In other aspects, a user may load the recesses 510 with the desired substances prior to collection of a sample. The recess may function similarly to the capillary chamber 140 in that it may draw fluid in an open position, remain sealed in a closed position, and dispense fluid to a receptacle or other container in a dispense position. In some examples, the recesses 510 may be arranged within a threshold angle of the capillary chamber. In one example, the threshold angle is less than 180 degrees; however, other angles may be used without departing from the scope of the present disclosure.

In one example, the recess or the recesses 510 may hold various substances (e.g., a reagent), chemically reactive with a sample drawn by the capillary chamber 140. The disc 120 may be rotated such that the recesses 510 and the capillary chamber 140 sequentially dispense their respective contents into a common container, such as the receptacle 102 of FIG. 1. As such, the contents may begin to mix and interact with one another once dispensed from disc 140 to the receptacle 102.

Turning now to FIG. 5B, it shows an embodiment 550 of the device 100 comprising the main body 110, the rotatable element (e.g., disc 120), and the capillary chamber 140. The embodiment 550 may be similar to the embodiment 500, except that one or more recesses or chambers 560 are arranged in a portion of the main body 110 through which the disc 120 rotates. As such, the disc 120 may be optionally free of the recesses 510. Additionally or alternatively, each of the disc 120 and the main body 110 may comprises respective recesses in some examples. As shown in FIG. 5B, the one or more recesses or chambers 560 may be located in a side wall 570 of the main body. While two recesses or chambers 560 are shown in one side wall 570, recesses or chambers 560 may be located in either or both side wall(s) of the main body 110. Such recesses may contain one or more substances useful for processing the collected liquid including, but not limited to, a reagent, enzyme, anticoagulant, and the like.

The embodiment 550 may comprise an additional position. More specifically, the embodiment 550 may comprise the open position, the sealed position, the dispense position, and one or more mixing positions. A number of mixing positions may be equal to a number of recesses arranged in the main body 110. A mixing position may comprise where the capillary chamber 140 is at least partially aligned with a recess of the recesses 560 so that a substance (e.g., a reagent) may interact with the sample in the capillary chamber 140 prior to the sample being dispensed into a container, such as the receptacle 102 of FIG. 1. In some examples, the receptacle 102 of FIG. 1 may include an additional substance, thus one or more of the same or different substances may be independently located in the capillary chamber, one or more of the recesses, and/or the receptacle.

Turning now to FIG. 6, it shows a method 600 for operating a disc having a rotating capillary chamber. In one example, the method 600 may be used with the device 100 of FIGS. 1A through 3C. In one example, the method 600 may be a method for collecting a fluid sample via the disc. In one example, the fluid sample is blood.

The method 600 begins at 602, where the method 600 includes rotating the capillary chamber to the open position, such as the open position of FIG. 3A. In the open position, the opening of the capillary chamber may be aligned with a first aperture of the disc (e.g., first aperture 152 of disc 110 of FIG. 1A). As such, the open position may be a position of the capillary chamber configured to aspirate a fluid. In some examples, the device may be set to the open position, in which case the method 600 would start at step 604.

The method 600 may proceed to 604 where the method may include contacting the capillary chamber opening to a surface of the fluid. Contacting the capillary chamber opening to the fluid surface may allow a capillary action to take place and promote fluid aspiration into the capillary chamber. The contacting may include touching the opening to the surface such that opening is minimally submerged into the fluid. By doing this, a likelihood of contamination of the fluid sample is reduced.

The method 600 may proceed to 606, where the method includes drawing a desired amount of fluid. As described above, the capillary chamber may comprise a coating to promote capillary action or to react with the sample. Additionally, the shape of the capillary chamber may promote self-ventilation so that air is forced out of the capillary chamber as fluid enters therein. A combination of the coating and the self-ventilation may allow the capillary chamber to quickly draw the desired amount of fluid corresponding to the volume of the capillary chamber. That is to say, an administrator collecting the fluid sample may select a disc comprising a capillary chamber having a volume sufficiently large to meet a desired amount of fluid. In some examples the capillary chamber may be constructed to capture a precise amount of fluid which may be the same or a smaller volume than the volume of the capillary chamber. As described above, the capillary chamber volumes may fall within a range from 1 pL to 50 μL.

The method 600 may proceed to 608, where the method includes determining if the capillary is filled to the desired volume. As an example, this may be a visual determination, wherein surfaces of the disc, the capillary chamber, and the main body are transparent. The capillary chamber may further comprise a marker indicating a fill line, wherein the fill line corresponds to the volume of the capillary chamber. As an example, if the capillary chamber comprises a 5 μL volume, then a fluid level in the capillary chamber touching the fill line may be exactly equal to 5 μL. If the fluid level is below the fill line, then the volume of fluid aspirated into the capillary chamber may be less than 5 μL. Additionally or alternatively, the capillary chamber may be filled to the desired volume following contact between the opening and the fluid surface lasting longer than a threshold time. In one example, the threshold time is a non-zero number (e.g., 5). The threshold time may be substantially equal to 5 seconds or less in some examples.

If the desired volume is not met, then the method may proceed to 610 to obtain a new fluid collection device. The method may return to 602 following 610. If the desired volume is met, then the method may proceed to 612 where the method may include moving the disc away from the fluid surface. The capillary chamber may be kept in the open position while moving the opening away from the fluid surface.

The method may proceed to 614, where the method may include rotating the capillary chamber to the closed position. As described above, rotating the capillary chamber from the open position to the closed position may include rotating the capillary chamber less than 180°. In one example, rotating the capillary chamber includes rotating the capillary chamber exactly 90° from the open position. In one example, rotating the capillary chamber from the open position to the closed position may include rotating the capillary chamber by some angle out of the open position so that the resulting position, which may be a closed position or a dispense position, is angled to the open position.

In some examples, 612 and 614 of the method 600 may be reversed such that rotating the capillary chamber to the closed position occurs prior to moving the capillary chamber away from the fluid surface. By doing this, a likelihood of contamination due to airborne particles may be decreased.

The method may proceed to 616, where the method may include determining if the body holding the disc is coupled to a receptacle. In some examples, coupling the body to the receptacle may include mating a threading of the body to a threading of the receptacle. Additionally or alternatively, the body may comprise a malleable material that may be compressed/deformed and inserted into the receptacle, wherein the material may expand/conform and press against interior surfaces of the receptacle. At any rate, the coupling between the body and the receptacle may hermetically seal such that contents within the receptacle are not in fluid communication with an ambient atmosphere.

If the body is not coupled to the receptacle, then the capillary chamber is maintained in the closed position and is not rotated to the open position or the dispense position. As such, the fluid sample in the closed position may not communicate with an ambient atmosphere or be dispensed. This may allow the disc to transport the fluid sample without risk of airborne particles coming into contact with the fluid sample. In other embodiments, the receptacle may comprise the main body 110 such that it is not necessary to attach an additional receptacle. In such embodiments, the capillary chamber may be rotated to the dispense position, depositing the fluid sample within the main body. In either configuration, the disc 120 may be locked into the desired position.

If the body is coupled to the receptacle, then the method may proceed to 620, where the method may include rotating the capillary chamber to the dispense position, similar to the position shown in FIG. 3C. In the dispense position, the capillary chamber may be facing a direction parallel to a direction of gravity, which may promote dispensing of the fluid sample from the capillary chamber to the receptacle. In one example, the dispensing may occur in response to an external pressure being applied to the disc and/or body (e.g., tapping the disc against a surface). Additionally or alternatively, a fluid in the receptacle may be used to contact the opening of the capillary chamber in the dispensing position, wherein surface tension forces of the fluid, in combination with the force of gravity, may draw out the fluid sample from the capillary chamber.

In this way, a rotating capillary chamber may be relatively small and easy to transport, while effectively capturing a fluid sample with or without exposure to additional reagents. The technical effect of including a rotating capillary chamber in a fluid collection device is to reduce a likelihood of contamination of the sample. Additionally, the capillary chamber may seal with the receptacle to prevent adulteration of the sample therein.

It will be appreciated that the configurations and routines disclosed herein are exemplary in nature, and that these specific embodiments are not to be considered in a limiting sense, because numerous variations are possible. The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A device for collecting a microfluidic sample, comprising:
   a rotating element held in a main body;
   wherein the rotating element consists of a capillary chamber with a single opening;
   wherein the capillary chamber is within a front surface, a back surface, and an outer edge of the rotating element, the front surface and the back surface of the capillary chamber are planar surfaces, and the opening is at the outer edge of the rotating element;
   wherein the capillary chamber is configured to draw a fixed amount of fluid in a single draw through the opening;
   wherein the rotating element is rotatably arranged within interior surfaces of the main body;
   wherein the capillary chamber rotates about an axis of rotation;
   wherein rotation of the rotating element rotates the capillary chamber between at least two positions; and
   wherein the at least two positions comprise an open and a closed position, wherein the capillary chamber is sealed from ambient exposure when in the closed position, and where the capillary chamber is open to ambient exposure when in the open position.

2. The device of claim 1, wherein the main body comprises at least one recess in a side wall, wherein the recess is sealed when the capillary chamber is in an open position.

3. A device for collecting a microfluidic sample, comprising:
   a rotating element held in a main body, wherein the rotating element consists of a capillary chamber with a single opening; and
   a receptacle shaped to receive fluid from the capillary chamber,
   wherein the capillary chamber is within a front surface, a back surface, and an outer edge of the rotating element, the front surface and the back surface of the capillary chamber are planar surfaces, and the opening is at the outer edge of the rotating element,
   wherein the capillary chamber is configured to draw a fixed amount of fluid in a single draw through the opening,
   wherein the rotating element is rotatably arranged within interior surfaces of the main body,
   wherein the capillary chamber rotates about an axis of rotation,
   wherein the receptacle is sealed from an ambient atmosphere and experiences no volume or pressure changes through the rotation of the capillary chamber, and
   wherein rotation of the rotating element rotates the capillary chamber to an open position and a dispense position, and where the open position fluidly couples the capillary chamber to the ambient atmosphere and fluidly seals the capillary chamber from the receptacle, and where the dispense position fluidly couples the capillary chamber to the receptacle and fluidly seals the capillary chamber from the ambient atmosphere.

4. A system, comprising:
   a rotating element comprising a capillary chamber with only one opening, wherein the opening is at an outer edge of the rotating element, wherein the rotating element is positioned to rotate within a main body, wherein an opening of the capillary chamber is wider than a bottom of the capillary chamber, wherein the opening and the bottom are both perpendicular to an axis of rotation, and wherein the capillary chamber draws fluid in a first position and dispenses fluid to a receptacle in a second position.

5. The system of claim 4, wherein the receptacle is fluidly sealed from an ambient atmosphere and experiences no pressure and volume changes through a rotation of the capillary chamber via the rotating element in the first position, the second position, and all other positions between the first position and the second position.

6. The system of claim 5, wherein the capillary chamber is fluidly sealed from the ambient atmosphere and the receptacle in all other positions between the first position and the second position.

7. The system of claim 4, wherein one or more of the rotating element, capillary chamber, and receptacle are transparent.

8. The system of claim 4, wherein the rotating element further comprises at least one additional chamber.

9. A device, comprising:
a capillary chamber within a disc and configured to rotate about an axis of rotation within a fixed plane, wherein at least two walls of the capillary chamber terminate together in an interior of the disc, the capillary chamber has a single opening, and wherein the opening is a widest portion of the capillary chamber; and
a receptacle comprising a reagent sealed from an ambient atmosphere during all rotational positions of the capillary chamber, and where the receptacle maintains a constant pressure and a constant volume;
wherein the device has no external venting.

10. The device of claim 9, wherein the capillary chamber rotates within interior surfaces of a main body, and where the interior surfaces brush against the opening of the capillary chamber to sweep fluid therefrom.

11. The device of claim 9, wherein the capillary chamber rotates to an open position fluidly coupling the capillary chamber to the ambient atmosphere, and where the capillary chamber draws a microfluidic sample in the open position when the opening of the capillary chamber is in contact with a surface of a fluid, a dispense position angled to the open position where the capillary chamber is fluidly coupled to the receptacle, and a plurality of sealed positions between the open position and the dispense position.

12. The device of claim 11, wherein the capillary chamber dispenses the microfluidic sample into the receptacle in the dispense position in response to an external pressure.

13. The device of claim 9, wherein the capillary chamber is coated with a substance for assisting in drawing a fluid into the capillary chamber and where the receptacle is coated with a substance that forms a reaction mixture with the fluid.

14. The device of claim 9, wherein the capillary chamber opens directly into the receptacle at at least one rotational position of the capillary chamber.

* * * * *